United States Patent
Zhu et al.

(10) Patent No.: US 9,613,874 B1
(45) Date of Patent: Apr. 4, 2017

(54) METHODS FOR EVALUATING SEMICONDUCTOR DEVICE STRUCTURES

(71) Applicant: Globalfoundries Singapore Pte. Ltd., Singapore (SG)

(72) Inventors: Jie Zhu, Singapore (SG); Binghai Liu, Singapore (SG); Eddie Er, Singapore (SG); Si Ping Zhao, Singapore (SG); Jeffrey Lam, Singapore (SG)

(73) Assignee: GLOBALFOUNDRIES SINGAPORE PTE. LTD., Singapore (SG)

( * ) Notice: Subject to any disclaimer, the term of this patent is extended or adjusted under 35 U.S.C. 154(b) by 0 days.

(21) Appl. No.: 14/985,178

(22) Filed: Dec. 30, 2015

(51) Int. Cl.
- *H01L 21/66* (2006.01)
- *G01R 31/26* (2014.01)
- *H01J 37/26* (2006.01)

(52) U.S. Cl.
CPC .............. *H01L 22/12* (2013.01); *H01J 37/26* (2013.01)

(58) Field of Classification Search
CPC ................................. H01L 22/12; H01J 37/26
USPC .......................................................... 438/16
See application file for complete search history.

(56) References Cited

U.S. PATENT DOCUMENTS

| | | | |
|---|---|---|---|
| 2010/0144069 A1* | 6/2010 | Johnson | G01R 31/2889 438/17 |
| 2015/0258769 A1* | 9/2015 | Farah | C30B 29/42 156/711 |

\* cited by examiner

*Primary Examiner* — David S Blum
(74) *Attorney, Agent, or Firm* — Lorenz & Kopf, LLP

(57) ABSTRACT

Methods for evaluating semiconductor device structures are provided. In one example, a method includes forming a support layer on a first side of a lamellar sample portion of the semiconductor device structure. The lamellar sample portion has a second side opposite the first side, a target analysis area on or proximate the first side, and a first thickness defined from the first side to the second side. The second side is milled to form a reduced thickness lamellar-supported sample portion that has a milled second side opposite the first side. The support layer is removed from the reduced thickness lamellar-supported sample portion to form a reduced thickness lamellar sample portion having a second thickness that is defined from the first side to the milled second side and that is less than the first thickness. The target analysis area of the reduced thickness lamellar sample portion is evaluated.

17 Claims, 3 Drawing Sheets

US 9,613,874 B1

METHODS FOR EVALUATING SEMICONDUCTOR DEVICE STRUCTURES

TECHNICAL FIELD

The technical field relates generally to semiconductor device structures, and more particularly to methods for evaluating semiconductor device structures including forming and evaluating an ultra-thin lamellar sample portion of the semiconductor device structure using, for example, a transmission electron microscopy (TEM) arrangement or the like.

BACKGROUND

Semiconductor devices, such as transistors or the like, are the core building block of a vast majority of electronic devices. In practice, it is desirable to accurately and precisely fabricate transistors and other semiconductor devices with physical features, critical dimensions, and/or other properties of the devices having specific physical dimensions, chemistries, crystalline structures or morphologies, and/or the like to thereby achieve semiconductor devices having their intended performance characteristics and/or to improve production yield. However, the hardware tools used to fabricate such devices may exhibit performance variations. As a result, semiconductor devices may be fabricated with features that deviate from their intended structure (e.g., physically and/or chemically), which in turn can lead to performance issues and/or reduced production yield. Therefore, it is desirable to evaluate the physical features, critical dimensions, chemistries, crystalline structures or morphologies, and/or other properties of the semiconductor devices.

One technique for evaluating the properties of semiconductor devices is transmission electron microscopy (TEM) analysis. TEM is a microscopy technique in which a beam of electrons is transmitted through a thin sample, with the electrons interacting with the sample as the electrons pass through. In general, various TEM analysis techniques allow for evaluation of a target analysis area (i.e., area intended to be analyzed or otherwise evaluated) of the sample including analysis of chemical identity, crystal orientation, electronic structure, and sample induced electron phase shift as well as the regular absorption based imaging of the target analysis area. For example, the interaction of the electrons transmitted through the sample can be used to form a TEM high resolution image of the target analysis area of the sample and/or for electron energy loss spectroscopy (EELS) for chemical analysis of the target analysis area.

However, sample thickness directly affects the image resolution and signal to noise ratio of TEM analysis. As a general rule, thinner samples provide better TEM image resolution and signal-to-noise ratios than thicker samples. In many TEM analysis techniques such as atomic scale high-resolution imaging and EELS analysis, sample thicknesses below 50 nm are desirable. Some conventional approaches for preparing samples of semiconductor device structures for TEM analysis include using focused ion beam (FIB) techniques to mill a portion of the semiconductor device structure into a lamellar (e.g., thin plate form) TEM sample. Unfortunately, it is very challenging to achieve a goal of forming a lamellar TEM sample having a uniform thickness of less than about 50 nm thickness across the target analysis area using such milling techniques. In particular, typically FIB uses a focused gallium (Ga+) ion beam to mill a lamellar TEM sample to a thickness of 60 to 100 nm. However, when the lamellar TEM sample becomes thinner than, for example, about 60 nm, it is challenging to continue milling the sample due to uneven stresses that develop in the sample and that can cause the sample to bend. Sample bending during milling can result in an uneven milling rate across the sample that can damage and prevent accurate evaluation of the target analysis area.

Accordingly, it is desirable to provide methods for evaluating semiconductor device structures including forming an ultra-thin lamellar sample portion of the semiconductor device structure having a relatively uniform thickness across its target analysis area for evaluation using, for example, a transmission electron microscopy (TEM) arrangement. Furthermore, other desirable features and characteristics will become apparent from the subsequent detailed description and the appended claims, taken in conjunction with the accompanying drawings and this background.

BRIEF SUMMARY

Methods for evaluating semiconductor device structures are provided herein. In accordance with an exemplary embodiment, a method for evaluating a semiconductor device structure includes forming a support layer on a first side of a lamellar sample portion of the semiconductor device structure. The lamellar sample portion has a second side opposite the first side, a target analysis area on or proximate the first side, and a first thickness defined from the first side to the second side. The second side is milled to form a reduced thickness lamellar-supported sample portion that has a milled second side opposite the first side. The support layer is removed from the reduced thickness lamellar-supported sample portion to form a reduced thickness lamellar sample portion having a second thickness that is defined from the first side to the milled second side and that is less than the first thickness. The target analysis area of the reduced thickness lamellar sample portion is evaluated.

In accordance with another exemplary embodiment, a method for evaluating a semiconductor device structure is provided. The method includes milling at least a portion of the semiconductor device structure to form a lamellar sample portion of the semiconductor device structure. The lamellar sample portion has a first side, a second side opposite the first side, a target analysis area on or proximate the first side, and a first thickness defined from the first side to the second side. Carbon is deposited on the first side of the lamellar sample portion to form a support layer on the first side. The second side is milled to form a reduced thickness lamellar-supported sample portion that has a milled second side opposite the first side. The support layer is etched from the reduced thickness lamellar-supported sample portion to form a reduced thickness lamellar sample portion having a second thickness that is defined from the first side to the milled second side and that is less than the first thickness. The target analysis area of the reduced thickness lamellar sample portion is evaluated.

In accordance with another exemplary embodiment, a method for evaluating a semiconductor device structure is provided. The method includes providing a lamellar sample portion of the semiconductor device structure. The lamellar sample portion includes silicon, oxide, or a combination thereof and has a first side, a second side opposite the first side, a target analysis area on or proximate the first side, and a first thickness defined from the first side to the second side. A support layer is formed on the first side of the lamellar sample portion. The support layer consists essentially of carbon. The second side is milled to form a reduced thickness lamellar-supported sample portion that has a milled second side opposite the first side. The support layer is exposed to a selective etching process that preferentially etches carbon over silicon and/or oxide to remove the support layer from the reduced thickness lamellar-supported sample portion and to form a reduced thickness lamellar sample portion having a second thickness that is defined from the first side to the milled second side and that is less than the first thickness. The target analysis area of the reduced thickness lamellar sample portion is evaluated using a transmission electron microscopy (TEM) arrangement.

BRIEF DESCRIPTION OF THE DRAWINGS

The various embodiments will hereinafter be described in conjunction with the following drawing figures, wherein like numerals denote like elements, and wherein.

DETAILED DESCRIPTION

Figure 1:
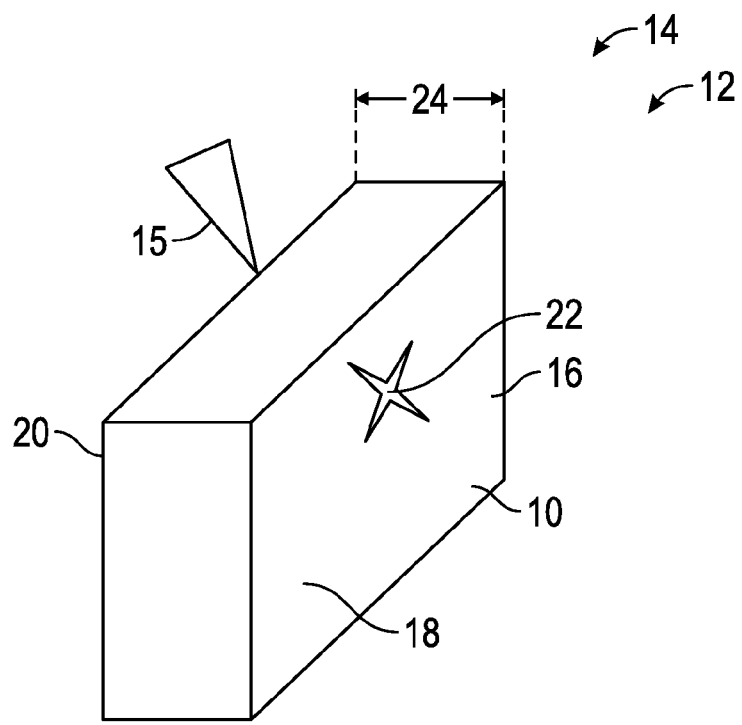
FIGS. 1-5 illustrate, in perspective side views, a portion(s) of a semiconductor device structure and a method for evaluating the semiconductor device structure in accordance with an exemplary embodiment.

The following Detailed Description is merely exemplary in nature and is not intended to limit the various embodiments or the application and uses thereof. Furthermore, there is no intention to be bound by any theory presented in the preceding background or the following detailed description.

Embodiments of the present disclosure are generally directed to methods for evaluating semiconductor device structures. For the sake of brevity, conventional techniques related to evaluating semiconductor device structures including, but not limited to, preparing sample portions of the semiconductor device structures for evaluation may not be described in detail herein. Moreover, the various tasks and process steps described herein may be incorporated into a more comprehensive procedure or process having additional steps or functionality not described in detail herein. In particular, various steps in evaluating semiconductor device structures are well-known and so, in the interest of brevity, many conventional steps will only be mentioned briefly herein or will be omitted entirely without providing the well-known details.

As described herein, methods for evaluating semiconductor device structures are provided. In an exemplary embodiment, a method for evaluating a semiconductor device structure includes milling at least a portion of a semiconductor device structure to form a lamellar sample portion. The lamellar sample portion has a first side, a second side opposite the first side, a target analysis area (e.g., area to be subject to TEM analysis at a later stage) on or proximate (e.g., within about 10 nm or less of the first side) the first side, and a first thickness that is defined from the first side to the second side. In an exemplary embodiment, the portion of the semiconductor device structure is milled (e.g., removing material from the portion) using a focus ion beam (FIB) milling process to form the lamellar sample portion having the first thickness of from about 400 to about 600 nm.

The method continues by forming a support layer on the first side of the lamellar sample portion of the semiconductor device structure of the lamellar sample portion. In an exemplary embodiment, the support layer covers the target analysis area. The second side of the lamellar sample portion is milled to form a reduced thickness lamellar-supported sample portion that has a milled second side opposite the first side. The support layer is removed from the reduced thickness lamellar-supported sample portion to form a reduced thickness lamellar sample portion having a second thickness that is defined from the first side to the milled second side and that is less than the first thickness. In an exemplary embodiment, the second side of the lamellar sample portion is milled using a focus ion beam (FIB) milling process to form the reduced thickness lamellar sample portion having the second thickness of about 30 nm or less.

In an exemplary embodiment, it has been found that by forming the support layer on the first side of the lamellar sample portion, the lamellar sample portion is well supported by the support layer during milling of the second side of the lamellar sample portion to substantially prevent development of uneven stresses and bending of the sample so as to form the reduced thickness lamellar sample portion having an ultra-thin and substantially uniform thickness (e.g., about 30 nm or less with a variation in thickness across at least the target analysis area of the reduced thickness laminar sample portion of less than about +/−3 nm) particularly across the target analysis area. As such, in an exemplary embodiment, the target analysis area of the reduced thickness lamellar sample portion can be evaluated, for example, using a transmission electron microscopy (TEM) arrangement to provide enhanced TEM image resolution and/or improved TEM signal-to-noise ratios for more accurately and precisely characterizing a physical feature(s), a critical dimension(s), chemistries, crystalline structure(s) or morphologies and/or one or more other properties of the semiconductor device structure.

FIG. 1 illustrates a portion 10 of a semiconductor device structure 12 of an electronic device 14 in accordance with an exemplary embodiment. The semiconductor device structure 12 may include one or more semiconductor devices (e.g., transistor, diode, an active region(s) of a semiconductor substrate, or the like), or a portion or portions of one or more semiconductor devices. As used herein, the term 'semiconductor substrate' will be used to encompass semiconductor materials conventionally used in the semiconductor industry from which to make electrical devices. Semiconductor materials include monocrystalline silicon materials, such as the relatively pure or lightly impurity-doped monocrystalline silicon materials typically used in the semiconductor industry, as well as polycrystalline silicon materials, and silicon admixed with other elements such as germanium, carbon, and the like. In addition, 'semiconductor material' encompasses other materials such as relatively pure and impurity-doped germanium, gallium arsenide, zinc oxide, glass, and the like. An exemplary semiconductor material is a silicon substrate. The silicon substrate may be a bulk silicon wafer or may be a thin layer of silicon on an insulating layer (commonly known as silicon-on-insulator or SOI) that, in turn, is supported by a carrier wafer.

In one embodiment, the portion 10 of the semiconductor device structure 12 includes a portion of an active region of a semiconductor substrate and/or at least a portion of a transistor such as, for example, a field effect transistor (FET) that includes source and drain regions, a channel region, a gate electrode, and a gate oxide (e.g., $SiO_2$ or the like) that is disposed between the channel region and the gate electrode. In an exemplary embodiment, the portion 10 of the semiconductor device structure 12 includes silicon (e.g., an active region of a semiconductor substrate) and/or oxide (e.g., gate oxide).

As illustrated, the portion 10 of the semiconductor device structure 12 is milled via a milling process 15 to form a lamellar sample portion 16. The lamellar sample portion 16 is configured having a thin plate form with a side 18 (e.g., first side), a side 20 (e.g., second side) opposite the side 18, and a target analysis area 22 (i.e., area intended to be analyzed or otherwise evaluated) on or proximate the side 18. In an exemplary embodiment, the lamellar sample portion 16 has a thickness (indicated by double headed arrow 24) defined from the side 18 to the side 20 of from about 400 to about 600 nm. In an exemplary embodiment, the milling process 15 is a focus ion beam (FIB) milling process.

Figure 2:
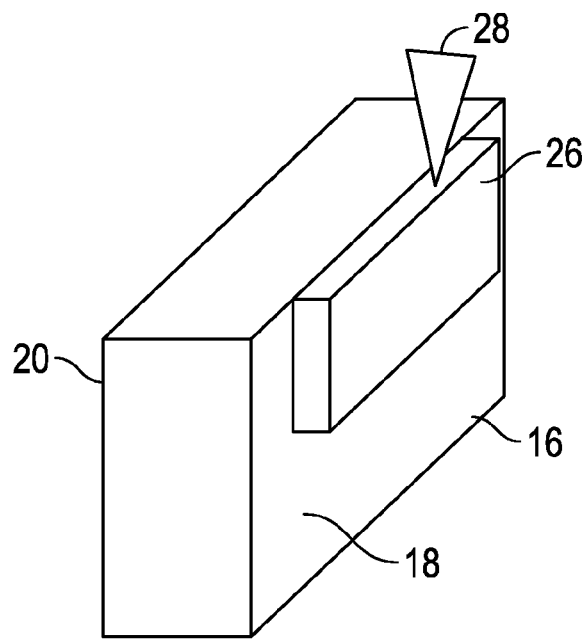

Referring to FIG. 2 with continued reference to FIG. 1, the method continues by forming a support layer 26 on the side 18 of the lamellar sample portion 16 using a deposition process 28. As illustrated, the support layer 26 is disposed on the side 18 covering the target analysis area 22. In an exemplary embodiment, the deposition process 28 includes depositing carbon on the side 18 to form the support layer 26. In embodiments, the support layer 26 consists essentially of carbon, i.e., the support layer 26 includes carbon as an essential component and may include other materials that do not materially affect the structure of the support layer 26. Alternatively, the support layer 26 may be formed of any carbonaceous materials that can be etched away using, for example, $Ar/O_2$ plasma etching.

In an exemplary embodiment, the deposition process 28 for forming the support layer 26 is an electron beam gas-injection process. In one example, the electron beam gas-injection process injects a precursor gas adjacent to (e.g., over, along, and/or across) the side 18 of the lamellar sample portion 16 and directs an electron beam through the precursor gas towards the side 18 to decompose the precursor gas and deposit the decomposition product of the gas onto the side 18. In an exemplary embodiment, the precursor gas is a carbon-containing gas (e.g., phenanthrene (e.g., $C_{14}H_{10}$) and the electron beam gas-injection process is conducted at conditions effective to generate an electron beam that decomposes the carbon-containing precursor gas to deposit carbon on the side 18 of the lamellar sample portion 16. In an exemplary embodiment, the operating conditions for the electron beam gas-injection process include, independently, a voltage of from about 1 to about 5 KeV, a current of from about 1.6 to about 3.2 nano-amperes, and a deposition time of from about 8 to about 12 minutes. Alternatively, the deposition process 28 may be a physical vapor deposition (PVD) process or the like.

In an exemplary embodiment, the support layer 26 is sized to provide additional support to the lamellar sample portion 16 so that the lamellar sample portion 16 can be subsequently further milled to an ultra-thin profile as discussed in further detail below without developing substantial bending stresses in the lamellar sample portion 16 during the additional milling step(s). In an exemplary embodiment, the support layer 26 has a layer thickness of from about 150 to about 250 nm, a width of from about 200 to about 500 nm, and a length of from about 200 to about 500 nm.

Figure 3:
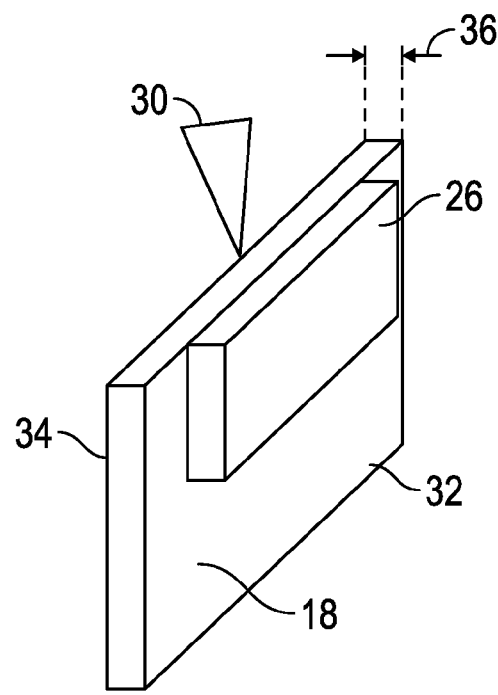

Referring to FIGS. 2-3, the process continues by milling the side 20 of the lamellar sample portion 16 using a milling process 30 to form a reduced thickness lamellar-supported sample portion 32. As illustrated, the reduced thickness lamellar-supported sample portion 32 has the first side 18 with the support layer 26 disposed thereon and a milled side 34 that is opposite the side 18. In an exemplary embodiment, the milling process 30 removes at least about 370 nm thickness of material from the side 20 of the lamellar sample portion 16 to form the reduced thickness lamellar-supported sample portion 32. In an exemplary embodiment, the reduced thickness lamellar-supported sample portion 32 has a thickness (indicated by double headed arrow 36) of about 30 nm or less, such as from about 10 nm to about 30 nm, for example from about 20 to about 30 nm. In an exemplary embodiment, the milling process 30 is a FIB milling process.

Figure 4:
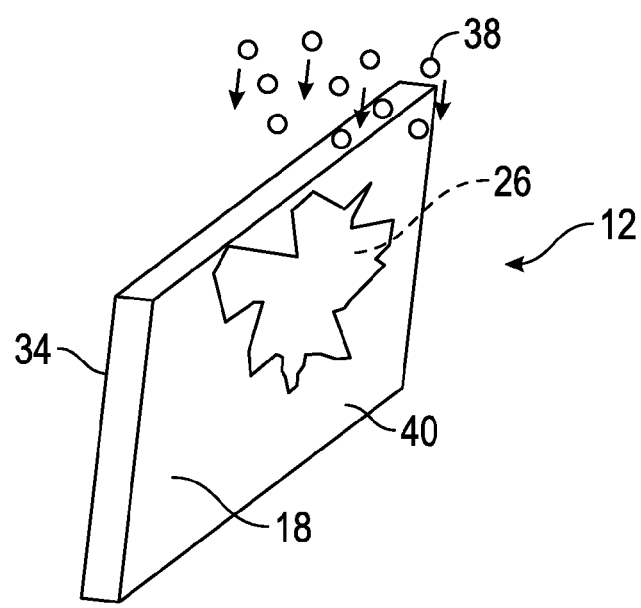

Referring to FIGS. 3-4, after forming the reduced thickness lamellar-supported sample portion 32, the support layer 26 is removed via an etching process 38 to form a reduced thickness lamellar sample portion 40. In an exemplary embodiment, the etching process 38 is a selective etching process that preferentially etches the support layer 26 without substantially etching or otherwise removing material from the reduced thickness lamellar-supported sample portion 32. As such, the thickness 38 of the reduced thickness lamellar-supported sample portion 40 (e.g., about 30 nm or less, such as from about 10 nm to about 30 nm, for example from about 20 to about 30 nm) will substantially match the thickness 36 of the reduced thickness lamellar-supported sample portion 32 (e.g., with a difference of +/−3 nm or less than +/−3 nm between the reduced thickness lamellar-supported sample portion 32 before and after etching). In one example, the reduced thickness lamellar-supported sample portion 32 includes silicon and/or oxide, the support layer 26 includes carbon, and the etching process 38 preferentially etches carbon over silicon and/or oxide to remove the support layer 26. In an exemplary embodiment, the etching process 38 is a plasma etching/cleaning process that uses oxygen and argon. In one example, the plasma etching/cleaning process uses a gas mixture ratio of oxygen to argon of from about 0.5:1.5 to about 1.5:0.5, for example about 1:1, to remove the support layer 26.

Figure 5:
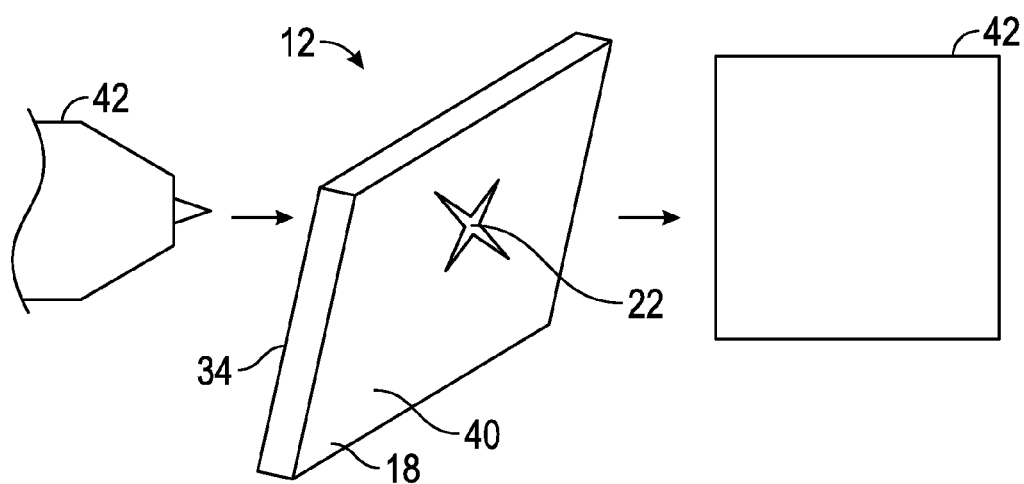

Referring to FIG. 5, the process continues by evaluating the target analysis area 22 of the reduced thickness lamellar sample portion 40. In an exemplary embodiment, the reduced thickness lamellar sample portion 40 is loaded or otherwise positioned in a transmission electron microscopy (TEM) arrangement 42 for analyzing the target analysis area 22. In one example, the TEM arrangement 42 provides a TEM high resolution image of the target analysis area 22. In another example, the TEM arrangement 42 is capable of electron energy loss spectroscopy (EELS) and provides chemical analysis of the target analysis area 22.

While at least one exemplary embodiment has been presented in the foregoing detailed description of the disclosure, it should be appreciated that a vast number of variations exist. It should also be appreciated that the exemplary embodiment or exemplary embodiments are only examples, and are not intended to limit the scope, applicability, or configuration of the disclosure in any way. Rather, the foregoing detailed description will provide those skilled in the art with a convenient road map for implementing an exemplary embodiment of the disclosure. It being understood that various changes may be made in the function and arrangement of elements described in an exemplary embodiment without departing from the scope of the disclosure as set forth in the appended claims.

What is claimed is:

1. A method for evaluating a semiconductor device structure, the method comprising:
    forming a support layer on a first side of a lamellar sample portion of the semiconductor device structure, wherein the lamellar sample portion has a second side opposite the first side, a target analysis area on or proximate the first side, and a first thickness defined from the first side to the second side, wherein forming the support layer comprises forming the support layer using a technique chosen from a physical vapor deposition (PVD) process or an electron beam gas-injection process;

milling the second side to form a reduced thickness lamellar-supported sample portion that has a milled second side opposite the first side;

removing the support layer from the reduced thickness lamellar-supported sample portion to form a reduced thickness lamellar sample portion having a second thickness that is defined from the first side to the milled second side and that is less than the first thickness; and evaluating the target analysis area of the reduced thickness lamellar sample portion.

2. The method of claim 1, wherein forming the support layer comprises forming the support layer on the first side covering the target analysis area.

3. The method of claim 1, wherein forming the support layer comprises using the electron beam gas-injection process at operating conditions effective to form the support layer.

4. The method of claim 3, wherein forming the support layer comprises providing a carbon-containing precursor gas to the electron beam gas-injection process.

5. The method of claim 3, wherein forming the support layer comprises using the electron beam gas-injection process at the operating conditions that include a voltage of from about 1 to about 5 KeV.

6. The method of claim 3, wherein forming the support layer comprises using the electron beam gas-injection process at the operating conditions that include a current of from about 1.6 to about 3.2 nano-amperes.

7. The method of claim 3, wherein forming the support layer comprises using the electron beam gas-injection process at the operating conditions that include a deposition time of from about 8 to about 12 minutes.

8. The method of claim 3, wherein forming the support layer comprises forming the support layer having a layer thickness of from about 150 to about 250 nm.

9. The method of claim 3, wherein forming the support layer comprises forming the support layer having a length and, independently, a width of from about 200 to about 500 nm.

10. A method for evaluating a semiconductor device structure, the method comprising:

forming a support layer on a first side of a lamellar sample portion of the semiconductor device structure, wherein the lamellar sample portion has a second side opposite the first side, a target analysis area on or proximate the first side, and a first thickness defined from the first side to the second side;

milling the second side to form a reduced thickness lamellar-supported sample portion that has a milled second side opposite the first side;

removing the support layer from the reduced thickness lamellar-supported sample portion to form a reduced thickness lamellar sample portion having a second thickness that is defined from the first side to the milled second side and that is less than the first thickness, wherein removing the support layer comprises removing the support layer using a plasma etching/cleaning process; and evaluating the target analysis area of the reduced thickness lamellar sample portion.

11. The method of claim 10, wherein removing the support layer comprises providing oxygen and argon to the plasma etching/cleaning process to remove the support layer.

12. A method for evaluating a semiconductor device structure, the method comprising:

milling at least a portion of the semiconductor device structure to form a lamellar sample portion of the semiconductor device structure, wherein the lamellar sample portion has a first side, a second side opposite the first side, a target analysis area on or proximate the first side, and a first thickness defined from the first side to the second side;

depositing carbon on the first side of the lamellar sample portion to form a support layer on the first side;

milling the second side to form a reduced thickness lamellar-supported sample portion that has a milled second side opposite the first side;

etching the support layer from the reduced thickness lamellar-supported sample portion to form a reduced thickness lamellar sample portion having a second thickness that is defined from the first side to the milled second side and that is less than the first thickness; and evaluating the target analysis area of the reduced thickness lamellar sample portion.

13. The method of claim 12, wherein milling the at least the portion of the semiconductor device structure comprises forming the lamellar sample portion having the first thickness of from about 400 to about 600 nm.

14. The method of claim 13, wherein milling the at least the portion of the semiconductor device structure comprises forming the lamellar sample portion using a focus ion beam (FIB) milling process.

15. The method of claim 12, wherein milling the second side comprises forming the reduced thickness lamellar-supported sample portion having the second thickness of about 30 nm or less.

16. The method of claim 12, wherein milling the second side comprises forming the reduced thickness lamellar-supported sample portion using a focus ion beam (FIB) milling process.

17. The method of claim 12, wherein milling the second side comprises removing at least about 370 nm thickness of material from the second side of the lamellar sample portion to forming the reduced thickness lamellar-supported sample portion.

* * * * *